US011538234B2

(12) United States Patent
Jones et al.

(10) Patent No.: US 11,538,234 B2
(45) Date of Patent: Dec. 27, 2022

(54) METHOD AND APPARATUS FOR DETERMINING INFORMATION ABOUT A DRUG-CONTAINING VESSEL

(71) Applicant: ARES TRADING S.A., Aubonne (CH)

(72) Inventors: Robert Jones, Cambridge (GB); Robert F. Marchington, Cambridge (GB); David Rimmer, Cambridge (GB); Bogdan-Alexandru Cociu, Cambridge (GB); William D. Addison, Cambridge (GB); Matthew J. Hayes, Cambridge (GB); Ruairi Duffy, Wroclaw (PL); Quentin Le Masne, Divonne les Bains (FR)

(73) Assignee: Ares Trading S.A., Aubonne (CH)

( * ) Notice: Subject to any disclaimer, the term of this patent is extended or adjusted under 35 U.S.C. 154(b) by 142 days.

(21) Appl. No.: 16/610,342

(22) PCT Filed: May 3, 2018

(86) PCT No.: PCT/EP2018/061401
§ 371 (c)(1),
(2) Date: Nov. 1, 2019

(87) PCT Pub. No.: WO2018/202804
PCT Pub. Date: Nov. 8, 2018

(65) Prior Publication Data
US 2020/0089989 A1    Mar. 19, 2020

(30) Foreign Application Priority Data
May 5, 2017 (EP) .................................... 17169781

(51) Int. Cl.
*G06V 10/75* (2022.01)
*A61M 5/24* (2006.01)
(Continued)

(52) U.S. Cl.
CPC ......... *G06V 10/751* (2022.01); *A61M 5/2459* (2013.01); *G06T 3/0012* (2013.01);
(Continued)

(58) Field of Classification Search
CPC .. G06K 9/6202; G06K 9/38; G06K 2209/057; G06K 9/621; G06K 2009/363;
(Continued)

(56) References Cited

U.S. PATENT DOCUMENTS

| | | | | |
|---|---|---|---|---|
| 2009/0278925 | A1* | 11/2009 | Koval | H04N 5/2624 348/92 |
| 2016/0243314 | A1* | 8/2016 | Rodiera Olive | A61B 5/4833 |
| 2018/0025239 | A1* | 1/2018 | Tsai | G06K 9/42 382/103 |

OTHER PUBLICATIONS

Recognition System of Medicine Bottle Label, Jiang et al, 2014, ids (Year: 2014).*

(Continued)

*Primary Examiner* — Jianxun Yang
(74) *Attorney, Agent, or Firm* — Carter, DeLuca & Farrell LLP; Carmella Stephens

(57) ABSTRACT

Information about a drug-containing vessel is determined by capturing image data of the curved surface of a cylindrical portion of a drug-containing vessel. The image data is unfurled from around the curved surface, binarised, and a template matching algorithm employed to determine that the label information comprises candidate information about the vessel and/or the drug.

11 Claims, 16 Drawing Sheets

(51) Int. Cl.
  *G06T 3/00* (2006.01)
  *G06T 3/40* (2006.01)
  *G06T 5/00* (2006.01)
  *G06V 10/28* (2022.01)

(52) U.S. Cl.
  CPC ............ *G06T 3/4038* (2013.01); *G06T 5/002* (2013.01); *G06V 10/28* (2022.01); *A61M 2205/3306* (2013.01); *A61M 2205/50* (2013.01); *A61M 2205/583* (2013.01); *A61M 2205/584* (2013.01); *A61M 2205/587* (2013.01); *A61M 2205/702* (2013.01); *G06T 2207/30004* (2013.01); *G06V 2201/034* (2022.01)

(58) Field of Classification Search
  CPC ... G06K 2209/01; G06K 9/36; A61M 5/2459; A61M 2205/3306; A61M 2205/50; A61M 2205/583; A61M 2205/584; A61M 2205/587; A61M 2205/702; G06T 3/0012; G06T 3/4038; G06T 5/002; G06T 2207/30004
  See application file for complete search history.

(56) References Cited

OTHER PUBLICATIONS

International Search Report and Written Opinion of the International Searching Authority, dated Jul. 4, 2018, corresponding to counterpart International Patent Application No. PCT/EP2018/061401.

Hui Xu et al., "A Study on the Automated Checking Method for Curved Label Image of Powder Medicine Bottle", 2017 3rd International Conference on Control, Automation and Robotics, Apr. 24, 2017; pp. 410-413.

Jiang et al., "Study of Highly Efficient Algorithms for the Character Recognition System of Medicine Bottle Label," Journal of Software, vol. 9, No. 4, Apr. 1, 2014; pp. 991-998.

Gu et al., "2000 fps Multi-Object Tracking Based on Color Histogram," Proceedings of SPIE, vol. 9025IS&T/SPIE Electronic Imaging, Feb. 2-6, 2014; Intelligent Robots and Computer XXXI: Algorithms and Techniques, vol. 8437; Apr. 26, 2012; pp. 84370E-1-84370E-13.

Larsen, "Individual Tree Top Position Estimation by Template Voting," Retried from the Internet, Jan. 1, 1999; 21st Canadian Symposium on Remote Sensing, Ottawa, Ontario, Canada, Jun. 21-24, 1999, 8 total pages.

* cited by examiner

METHOD AND APPARATUS FOR DETERMINING INFORMATION ABOUT A DRUG-CONTAINING VESSEL

FIELD

This disclosure relates to the determination of information about a drug-containing vessel. In particular, but without limitation, this disclosure relates to a method and apparatus for determining information about a drug-containing vessel (primary pack) such as a syringe or cartridge that is contained within a medical device such as an autoinjector.

BACKGROUND

Patients that suffer from one or more of a variety of medical conditions such as multiple sclerosis, arthritis, growth hormone deficiency, Turner Syndrome, and chronic renal failure may require regular percutaneous administration of one or more medicaments. Although such administration may be performed by health professionals, in some cases administration may be performed by the patient themselves or their carer. Some medical devices, such as autoinjectors, are operable to receive a drug-containing vessel, such as a syringe or cartridge, and, upon actuation, percutaneously administer the drug to the patient.

SUMMARY

Aspects and features of the present disclosure are set out in the appended claims

BRIEF DESCRIPTION OF THE DRAWINGS

Examples of the present disclosure will now be explained with reference to the accompanying drawings in which.

DETAILED DESCRIPTION

Once a drug-containing vessel has been loaded into a medical device, such as an auto injector, it is to be expected that the user will attempt to actuate the device so as to administer the drug. However, if the wrong drug-containing vessel is loaded into the medical device, then the patient may not receive the drug that they need, may receive the wrong dosage of the drug, or may receive a drug that it is not appropriate for them to receive—all of which can be seriously deleterious to the patient. Checking whether a drug-containing vessel is the correct one for a patient is generally done by visually inspecting a label borne on the curved surface of a cylindrical portion of the drug-containing vessel. Although drug-containing vessels could be mechanically configured, for example by way of keying, so as to make them recognisable from their shape, and/or could be provided with other identification means—such as RFID tags, the fact that different manufacturers produce drugs and provide them in differently shaped containers means that visual inspection of the containers' labels is currently the best approach for verifying the contents of a drug-containing vessel.

In an alternative embodiment, after use the patient will discard the drug-containing vessel. Discarding of the drug containing vessel may be carried out using a vessel configured to receive such discarded empty drug vessel. In order to improve compliance monitoring the discard vessel may need to recognize the empty drug-containing vessel. So in an alternative embodiment the invention is directed to a device and method for recognizing and identifying the drug-containing vessel such as to be able to record the drug containing vessel that is disposed of and its identity.

There is described herein an approach for determining information about a drug-containing vessel that is carried by the curved surface of a cylindrical portion of a drug-containing vessel so that a drug-agnostic medical device, such as an auto injector, can determine which drug has been loaded into it and can hence determine whether or not to enable administration of the drug.

Figure 1:
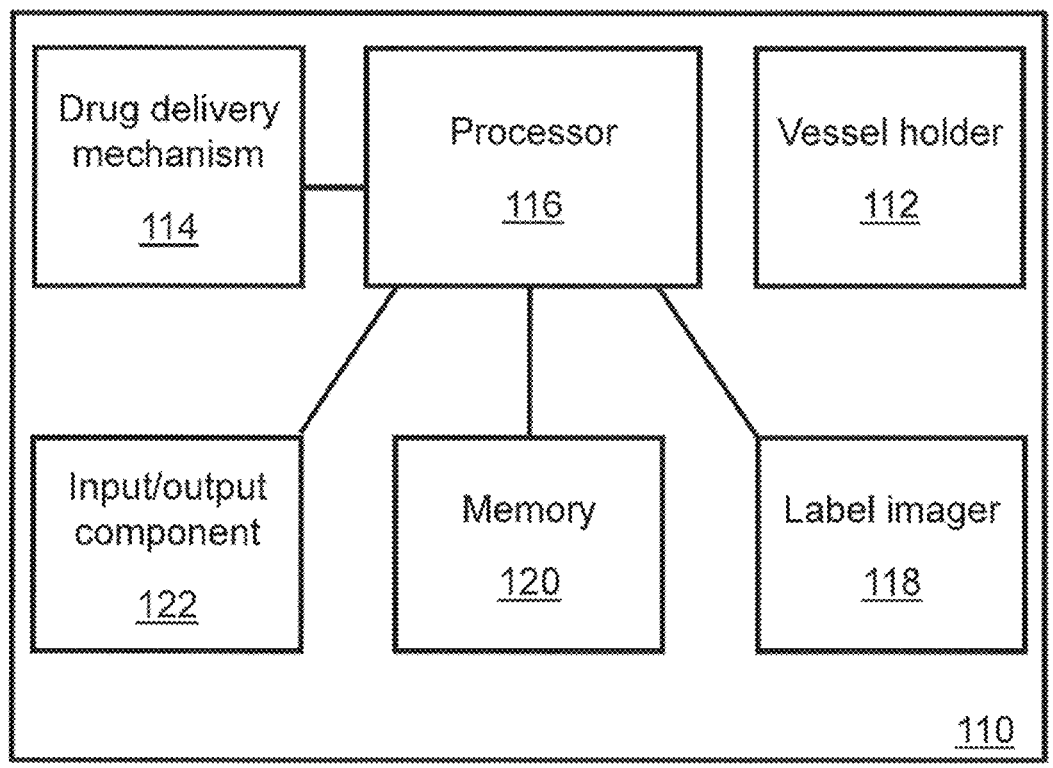
FIG. 1 shows a medical device.
Figure 2:
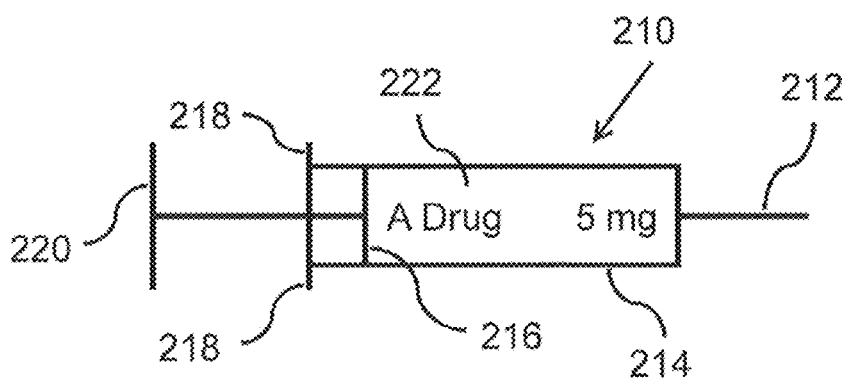
FIG. 2 shows an example drug-containing vessel.
Figure 3:
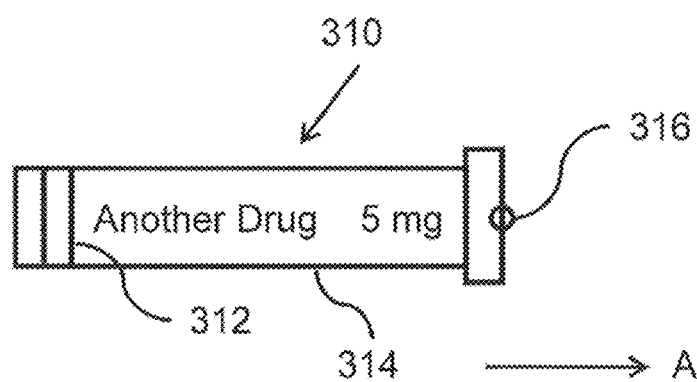
FIG. 3 shows alternative drug-containing vessel.

FIG. 1 shows a medical device 110 a vessel holder 112 arranged to hold a containing vessel such as a syringe or a cartridge. A drug delivery mechanism 114 is operable to act with a drug-containing vessel held by the vessel holder 112 so as to administer the drug contained in that vessel when the medical device is adjacent to the patient (not shown) and the drug delivery mechanism 114 is instructed to do so by a processor 116. The drug delivery mechanism being operable to move at least a part of the vessel holder 112 along with the drug-containing vessel and a needle coupled thereto along a path from within the interior of the medical device 110 to the exterior of the medical device 110 so as to puncture a patient's dermis. The drug delivery mechanism 114 is further operable to depress a plunger of the drug-containing vessel so as to cause the drug contained thereby to be expelled from the drug-containing vessel and via the hypodermic needle into the patient's tissue. The medical device 110 further comprises a label imager 118 operable to image a label borne on a curved surface of a cylindrical portion of the drug-containing vessel and to provide image data consequent to that imaging to the processor 116. The processor 116 is arranged to operate in accordance with instructions stored in memory 120 so as to receive images from the label imager 118 and to control the drug delivery mechanism 114. Processor 116 may further be coupled to an input/output component 122 by which the processor 116 may receive instructions for example template information with regard to drugs and dosages associated with the medical device and/or may output alarms, for example to indicate that an unexpected drug-containing vessel has been inserted into the medical device 110. FIG. 2 shows an example drug-containing vessel 210 which is a syringe having: a hypodermic needle 212, a cylindrical portion 214, a plunger 216, finger guards 218, and an actuation end 220. The cylindrical portion 214 of the syringe 210 bears a label that was rectangular but has been wrapped around the curved surface of the cylinder. The label 222 contains information about the drug contained by the syringe 210 and further contains information about the amount of drug contained by the syringe—in this case "5 mg". FIG. 3 shows alternative drug-containing vessel 310—in this case a cartridge having a plunger 312 operable to slide within in a cylindrical portion of the cartridge 314 so that, when a needle pierces a pierceable membrane 316 and the plunger is moved in direction A, the drug is expelled via the needle.

A number of different approaches for imaging labels borne by the curved surfaces of the vessel the cylindrical portions of drug-containing vessels have been contemplated and will now be described.

Scanning Imaging Devices

Figure 4:
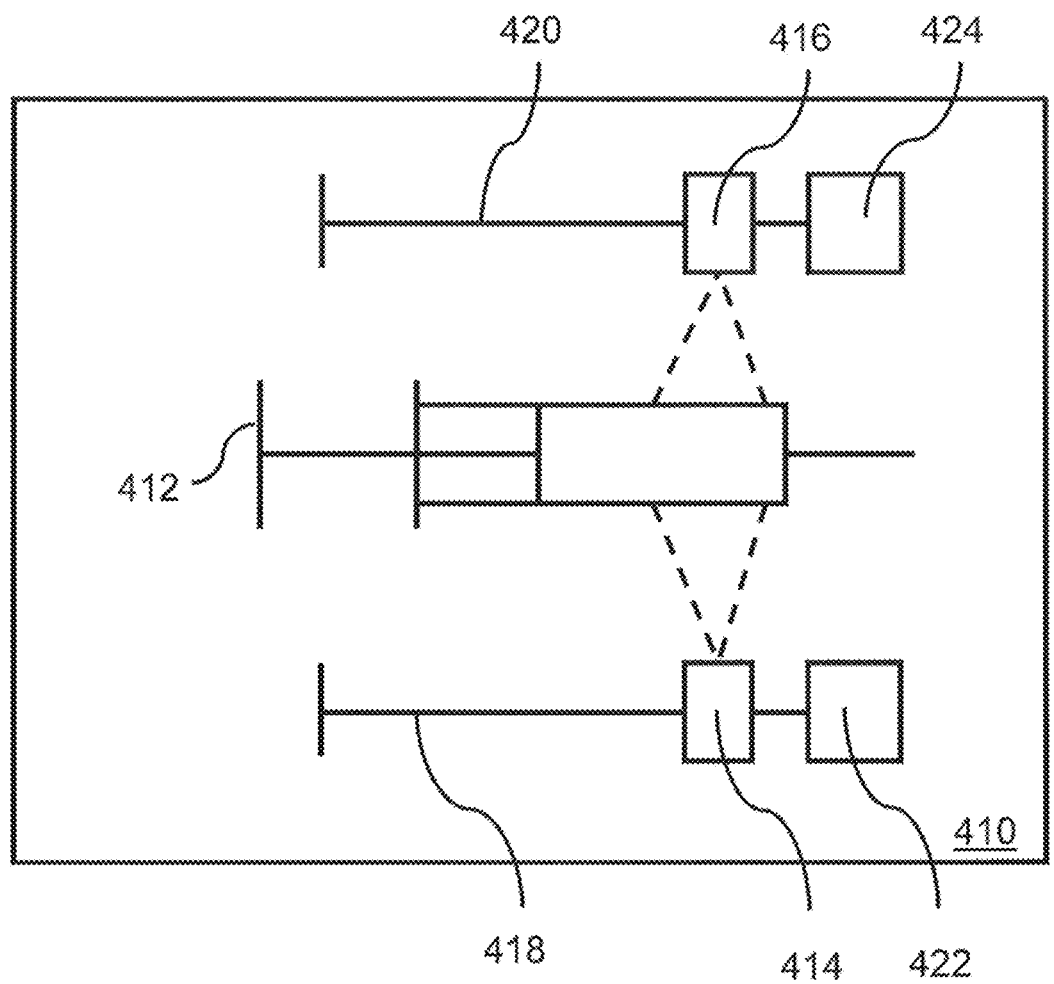
FIG. 4 shows a medical device carrying a drug-containing vessel.

FIG. 4 shows a medical device 410 carrying a drug-containing vessel (in this case a syringe) 412. The medical device 410 has a pair of imaging devices 414, 416 operable to move along respective rails 418, 420 upon actuation of respective actuators 422, 424 in direction B-C or C-B so as to enable the imaging devices 414, 416 to capture a plurality of images of opposite sides of the curved surface of the cylindrical portion of the drug-containing vessel 412. Imaging devices 414, 416 form part of the label imager 118 and consequently relay the acquired images as image data to the processor 116.

Once received by the processor 116, images from each imaging device that were acquired at different time points as that imaging device moved along its rail may be fused or blended so as to produce a single image from each imaging device for subsequent processing.

Although the example of FIG. 4 uses a pair of imaging devices mounted on rails, approaches are also contemplated wherein the number of imaging devices is greater than two, for example any of three to ten or even more. Furthermore, the imaging devices need not be mounted on rails and alternative mechanisms could be employed in order to enable them to scan the cylindrical portion of the drug-containing vessel 412.

Hall of Mirrors

Figure 5:
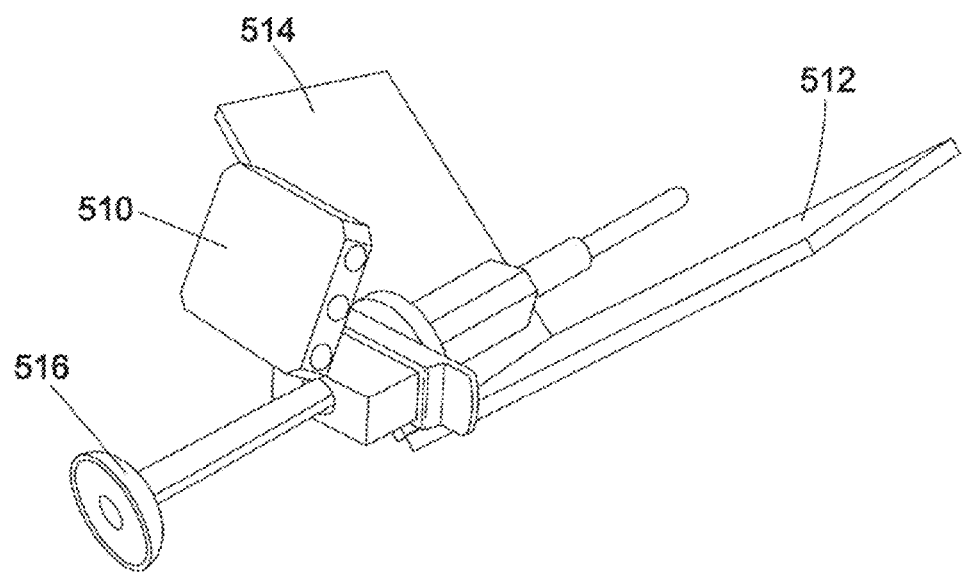
FIG. 5 shows an example set up for whereby a single imaging device may be used in conjunction with a pair of mirrors.
Figure 6:
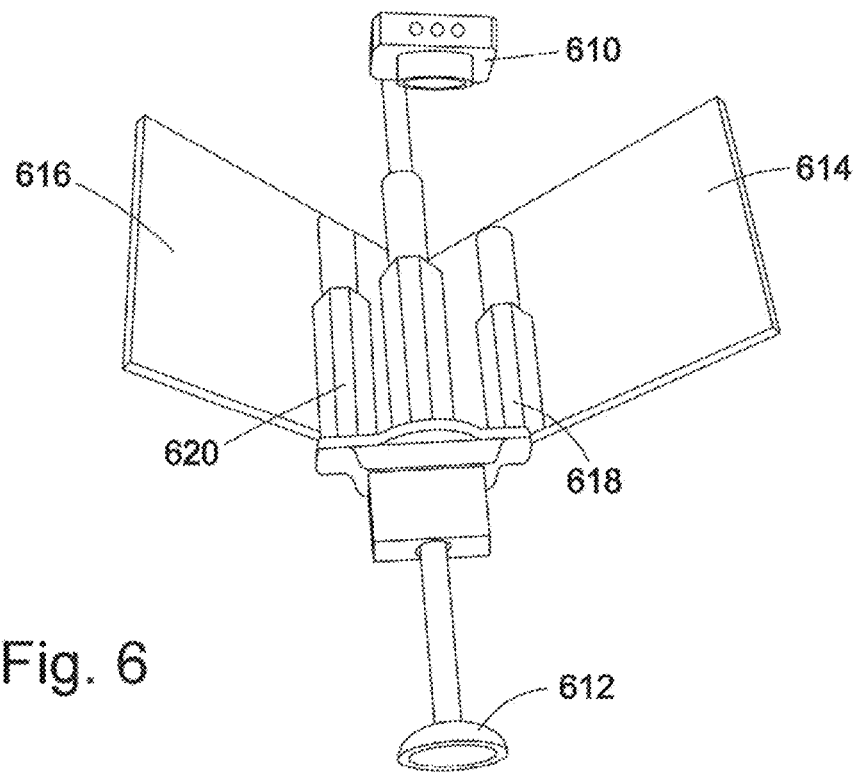
FIGS. 6 and 7 show an alternative arrangement using a "hall of mirrors" principal.
Figure 7:
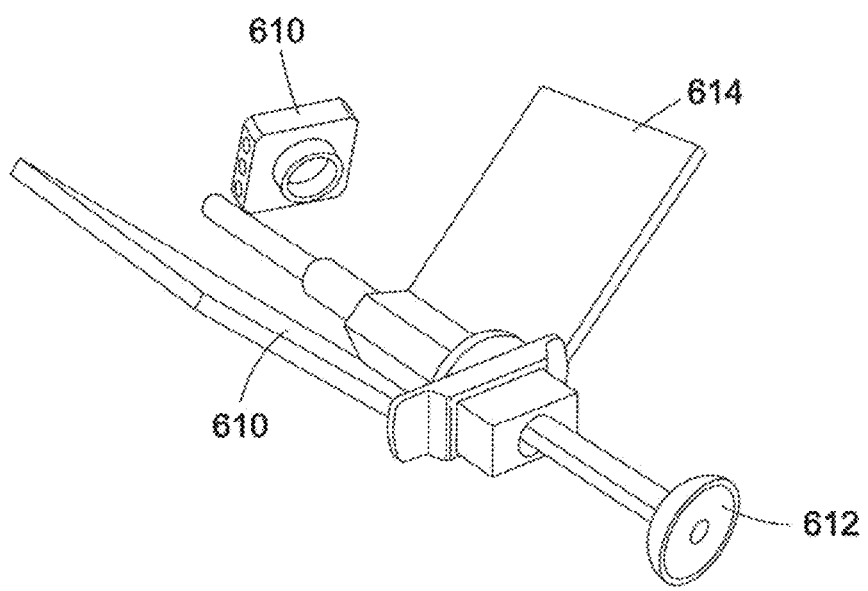

FIG. 5 shows an example set up whereby a single imaging device 510 may be used in conjunction with a pair of mirrors 512, 514 to image a drug-containing vessel 516 using the "hall of mirrors" approach. Advantageously this approach avoids the imaging device needing to be near the end of the needle and so does not interfere with moving the needle towards a patient's skin or actuation of the plunger of the drug-containing vessel. However for some drug-containing vessels (such as those having syringe flanges) portions projecting from the drug-containing vessel can obscure parts of the label. FIGS. 6 and 7 show an alternative arrangement using a "hall of mirrors" principal whereby an imaging device 610 is positioned near the tip of a needle of a drug-containing vessel 612 that is positioned adjacent to a pair of mirrors 614, 616 whose planes are angled with respect to one another. In FIG. 6, reflections of the drug-containing vessel 612 can clearly be seen at positions 618 and 620.

Figure 8:
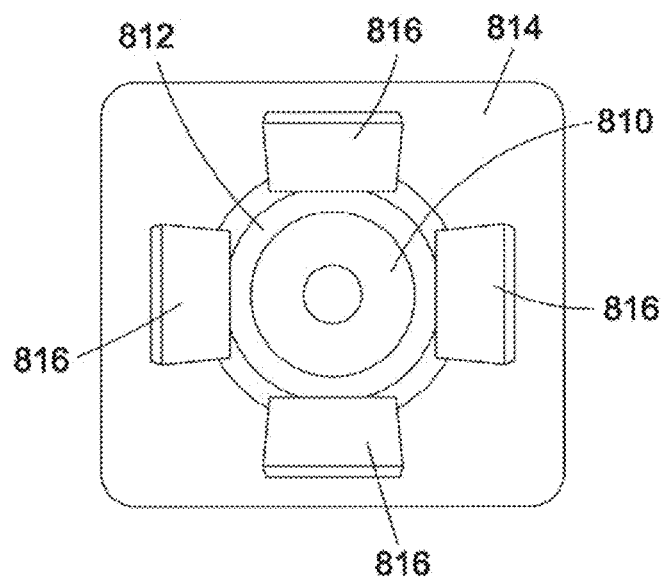
FIG. 8 shows an end on view of a drug-containing vessel and mirror setup.
Figure 9:
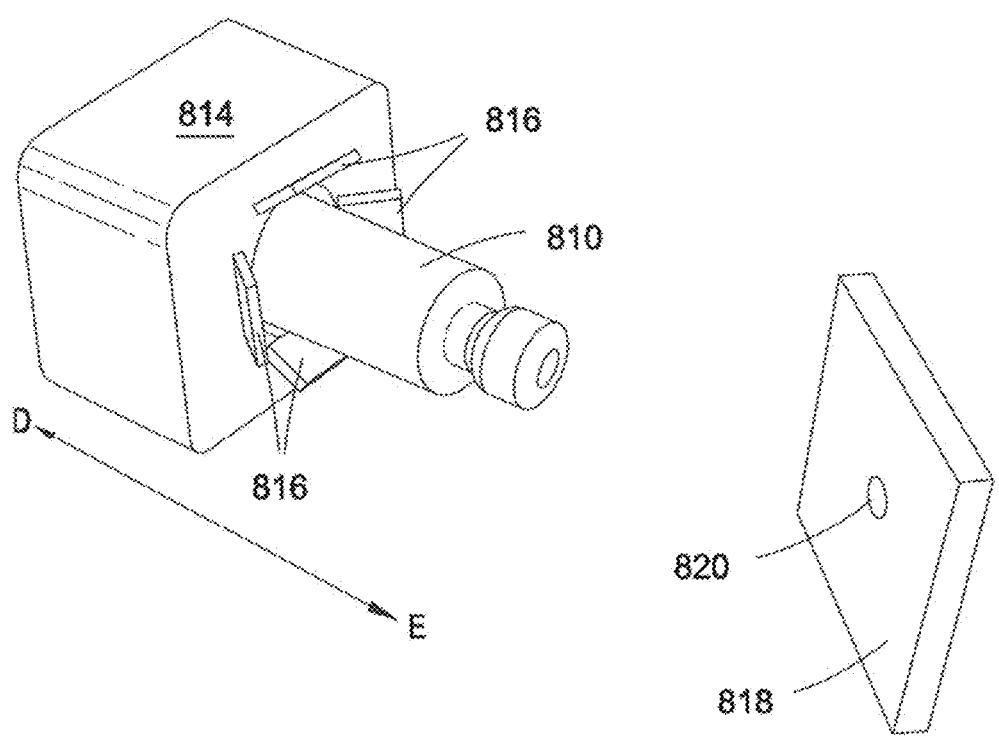
FIG. 9 shows a perspective view of the setup of FIG. 8.

FIG. 8 shows an end on view of a drug-containing vessel 810 (in this case a cartridge) that lies within a hole 812 of a block 814 that is arranged to translate over the drug-containing vessel 810 in direction D-E and E-D of FIG. 9. The block 814 further comprises a plurality of mirrors 816 angled away from the long axis of the drug-containing vessel 810 so that, when the block 814 is translated in direction D-E or E-D and an imaging device (not shown in either of FIG. 8 or 9), images a mirror that is placed at an angle (in this case 45°) with respect to the direction D-E, the curved surface of the cylindrical portion of the drug-containing vessel 810 is scanned and imaged. As the mirror 818 lies along the path that a needle connected to the drug-containing vessel 810 would traverse in order to exit the medical device, an elliptical hole 820 is provided in the mirror 818.

Hybrid Approach

Figure 10:
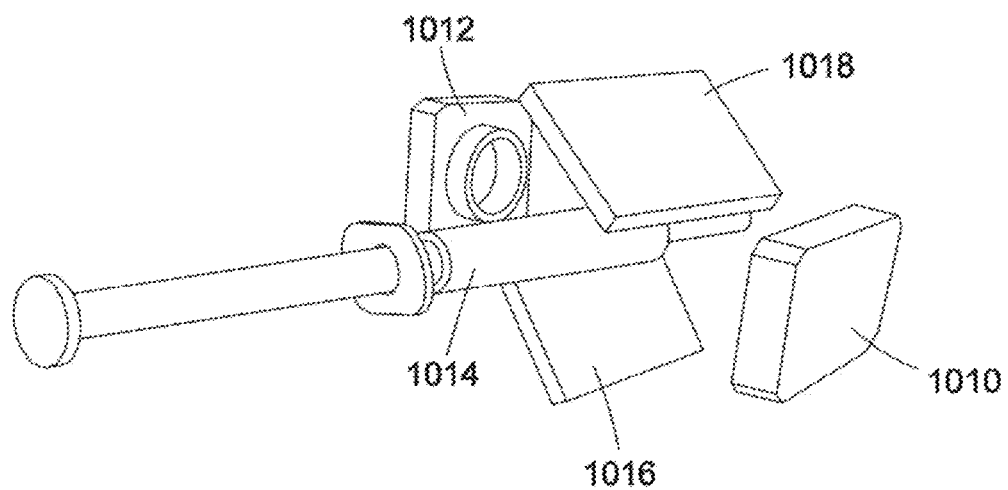
FIG. 10 shows a hybrid approach wherein a plurality of imaging devices are arranged both to image directly a drug-containing vessel and also to image respective mirrors.

FIG. 10 shows a hybrid approach wherein a plurality of imaging devices 1010, 1012 are arranged both to image directly a drug-containing vessel 1014 and also to image respective mirrors 1016, 1018 that are positioned so that each respective imaging device sees a reflective portion of the curved surface of the drug-containing vessel 1014. In this instance the imaging devices 1010, 1012 are arranged diametrically opposite one another with respect to a long axis of the drug-containing vessel 1014 and the mirrors 1016, 1018 are arranged diametrically opposite one another with respect to the long axis of the drug-containing vessel 1014 and at an angle (in this case 45°) so that each imaging device is able to acquire images of the drug-containing vessel from two different perspectives.

Image Unfurling

Figure 11:
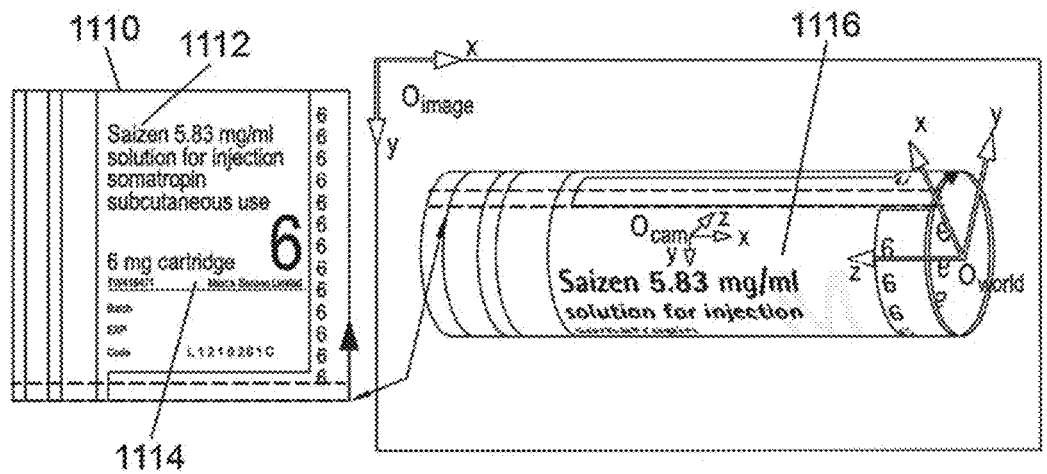
FIG. 11 shows an example label for a drug-containing vessel.

Labels that are applied to drug-containing vessels can either be adhesive labels that are printed on before being furled around the curved surface of the cylindrical portion of a drug-containing vessel or may be printed or otherwise placed on the curved surface of the cylindrical portion of a drug-containing vessel. FIG. 11 shows an example label 1110 for a drug-containing vessel containing information about the drug 1112, in this case that the drug is "saizen 5.83 mg/ml" and the label 1110 further contains information 1114 about the drug-containing vessel, in particular that it is a "6 mg cartridge". FIG. 11 further shows label 1110 when it has been furled around a curved surface corresponding to the curved surface of a cylindrical portion of a drug-containing vessel 1116. When imaged, such a furled label will have portions of the label information that it contains foreshortened—for example the words "somatropin 118" are foreshortened in the furled label 1116 of FIG. 11 to the point where they are difficult to discern. Accordingly, in order for an image of a drug-containing vessel to have label information extracted therefrom whilst avoiding or reducing the effects of label information foreshortening, a relationship between the original rectangular label (which may be a hypothetical original rectangular label in the event that the label information was directly printed onto the drug-containing vessel and the data received by an imaging device imaging the drug-containing vessel needs to be established. The matter is somewhat confounded by the fact that, due to the label have being furled about a cylinder, a projection on the acquisition point of an imaging device from the curved surface of the cylindrical portion of the drug-containing vessel will often coincide with two points on the label—one from a near side to the imaging device and one from a far side to the imaging device.

Figure 12:
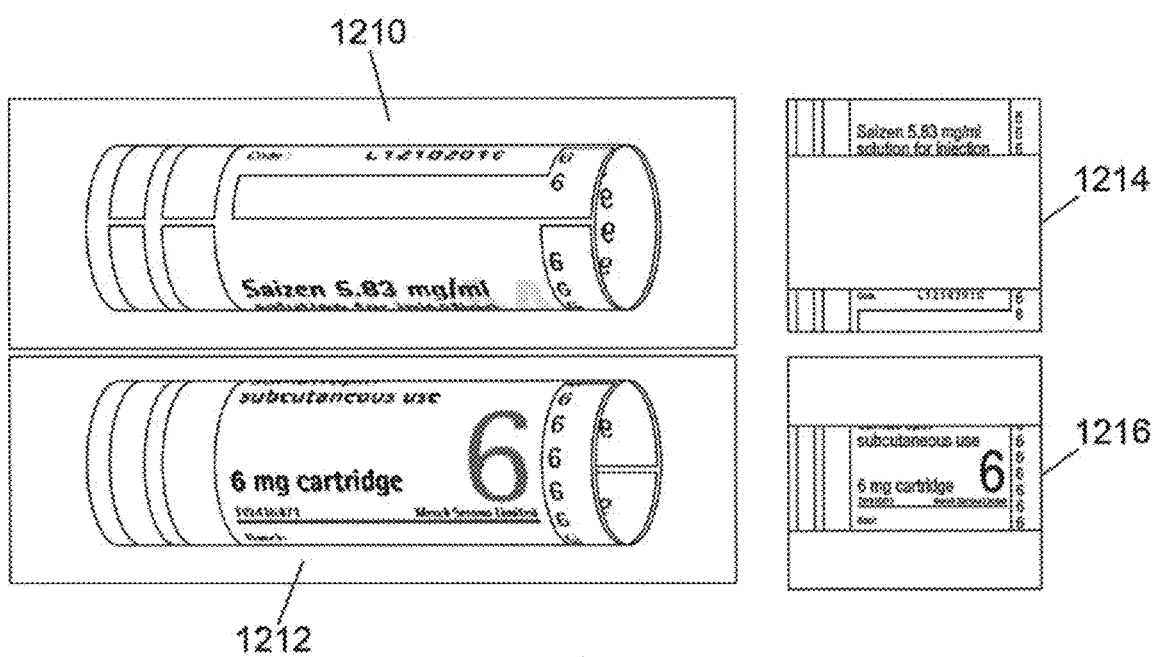
FIG. 12 shows a pair of example perspective views of a rectangular label that has been wrapped around the curved surface of a cylindrical portion of a drug-containing vessel.

FIG. 12 shows a pair of example perspective views of a rectangular label that has been wrapped around the curved surface of a cylindrical portion of a drug-containing vessel. On the left of FIG. 12, the two perspective views 1210, 1212 illustrate that respective portions of the label are not visible due to the other portions of the label being in front of them. Accordingly, when the information from an imaging device that acquires such a perspective image is unfurled so as to set it out as a rectangular label 1214, 1216 not all of the label can be reconstructed. Accordingly, one approach, which may be optional, for unwrapping a label from the curved surface of the cylindrical portion of a drug-containing vessel includes removing mappings that would be obscured from the imaging device by other portions of the label that lie in front thereof. However, as drug-containing vessels and the drugs contained therein are sometimes somewhat transparent, a further approach may instead keep that information and look to use it to help read the label.

Figure 13:
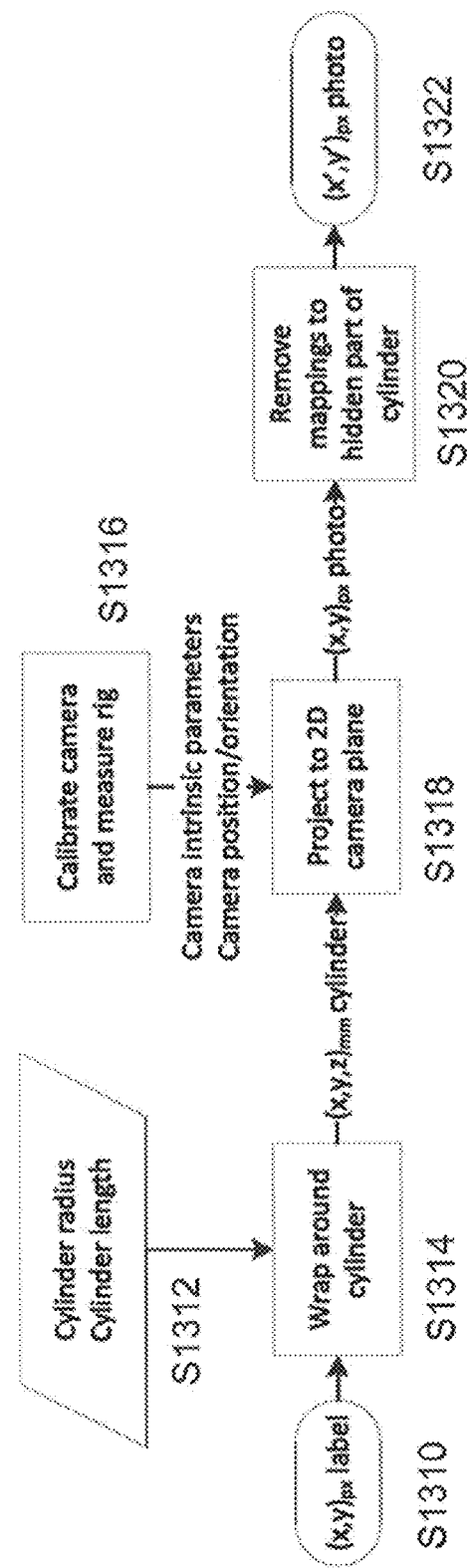
FIG. 13 illustrates how x and y pixel coordinates of a rectangular label translate into imaging device coordinates.

FIG. 13 illustrates how x and y pixel coordinates of a rectangular label translate into photo (or imaging device) coordinates. In particular, taking at step s1310 a set of x, y pixel labels of the rectangular label, and taking into account from step s1312 the expected cylinder radius and cylinder length of the cylindrical portion of the drug-containing vessel, at step s1314, the pixel labels can be wrapped around the cylinder so as to project them into 3D world coordinates. Following a calibration step s1316 to calibrate the imaging device and the device within which both the imaging device and the vessel holder are positioned, at step s1318, the 3D world coordinates can be projected onto a 2D imaging device plane before, at step s1320, mappings to portions of the curved surface of the cylinder that would be obscured from the view of the imaging device can be removed so as to produce as an output at step s1322 a locations in the photo that correspond to the x,y pixel positions in the label image. Once it is known where any pixel in the rectangular label will map onto in an image of the cylinder, each pixel in the rectangular label can be sampled in the imaging device image in order unfurl the imaging device image. As the locations in the imaging device image that are to sampled will not necessarily coincide with integer pixel locations, interpolation approaches, such as nearest neighbour, bilinear, and/or higher order approaches such as b-spline interpolation, can be used in order to interpolate the imaging device image.

As an example, the size of the label is obtained from the cylinder length and radius parameters: height=2*pi*radius, width=length. A size of the image in pixels is obtained by scaling this considering the desired resolution of the recreated label in DPI (dots per inch). The label is then wrapped around a cylinder in a 3D world. The origin of the world coordinate system is chosen such that it coincides with the centre of the circle in the base of the cylinder. Axes x and y are then in the plane containing this circle, while the z axis is along the length of the cylinder. The x axis can point to where the label is "glued", which corresponds to the bottom line of the label 1116. From this line upwards, each line of the label is placed on the circle at an angle increasing anticlockwise. The wrapping, or mapping from (x,y) of the label in pixels to (x,y,z) of the cylinder in millimetres is performed as:

$$x_{cylinder} = r_{cylinder} \cos\left(\frac{y\max - y}{y\max} \times 2\pi\right)$$

$$y_{cylinder} = r_{cylinder} \sin\left(\frac{y\max - y}{y\max} \times 2\pi\right)$$

$$z_{cylinder} = \frac{x\max - x}{labelwidth_{px}} \times labelwidth_{mm}$$

This operation is carried out for each (x,y) pixel for the given label size and gives a physical location (in mm) in the world for each pixel.

Given a cylinder existing in the world, it is desired to estimate where each of its (x,y,z) voxels would appear when a photo of it is taken from a known position, with an imaging device of known parameters. FIG. 11 also shows the image coordinate system and its origin in the top left corner of the image. The mapping from world to photo pixels can be found as:

$$\begin{bmatrix} u \\ v \\ w \\ 1 \end{bmatrix} = P \begin{bmatrix} x_{cyl} \\ y_{cyl} \\ z_{cyl} \\ 1 \end{bmatrix}, x_{photo} = \frac{u}{w}, y_{photo} = \frac{v}{w}$$

Here P is a 4×4 homogenous imaging device transformation matrix:

$$P = K \begin{bmatrix} R & T \\ 0\ 0\ 0 & 1 \end{bmatrix}$$

Intrinsic imaging device Parameters (K matrix): K is the matrix containing the intrinsic imaging device parameters, and depends on the imaging device focal length, on the sensor size and on the position of the optical centre. It is essentially a scaling and translation matrix that brings millimetre coordinates to pixel coordinates and accounts for the optical centre (centre of image) not corresponding to the photo origin (which is in the top left corner). The parameters depend on the imaging device in use, and a person skilled in the art have be well acquainted with the use of calibration objections (such as checkerboards) in order to determine focal lengths $f_x$ and $f_y$ in order to determine K. In this case, K is:

$$K = \begin{bmatrix} \frac{f_x}{s_x} & 0 & 0 & O_x \\ 0 & \frac{f_y}{s_y} & 0 & O_y \\ 0 & 0 & 1 & 0 \\ 0 & 0 & 0 & 1 \end{bmatrix}$$

Where $s_x$ and $s_y$ are pixel sizes in millimetres, and $O_x$ and $O_y$, are the pixel coordinates of the optical centre in the image (which should be around the actual centre of the image, but does not coincide with it).

Lens distortion parameters may also be obtained from the imaging device calibration process and used to adjust K accordingly.

Extrinsic Imaging Device Parameters (R and I matrices): as the world coordinate system does not coincide with the imaging device coordinate system (located in the optical centre, with axes as pictured in FIG. 11), the transformation expressed by rotation matrix R and translation vector T is required, such that the world points are expressed with respect to the imaging device axes. A more intuitive manner of specifying the imaging device location can been employed that is tailored to the image coordinate system. The parameters to be specified to obtain the R and T matrices are:

the physical location of the imaging device in world coordinates (eye vector);
the coordinates of the point at which the imaging device is looking (centre vector);
a direction in the world which, when projected on the image plane, would point up, e.g. the world y axis (up vector). Considering eye, centre, and up as row vectors, the R matrix is obtained through the following steps:

$$\vec{L} = \overrightarrow{centre} - \overrightarrow{eye}; \vec{L_N} = \frac{\vec{L}}{\|\vec{L}\|};$$

$$\vec{s} = \vec{L_N} \times \overrightarrow{up}; \vec{s_N} = \frac{\vec{s}}{\|\vec{s}\|};$$

$$\overrightarrow{up'} = -\vec{s_N} \times \vec{L_N};$$

$$R = \begin{bmatrix} \vec{s_N} \\ \overrightarrow{up'} \\ \vec{L_N} \end{bmatrix};$$

and the imaging device translation with respect to the newly rotated coordinate system is:

$$T = -R * \overrightarrow{eye}^T$$

This can also be understood by first applying a translation described by $\overrightarrow{eye}$ followed by the rotation described by R.

Removing mappings to the hidden part of the cylinder: in a single image and assuming that the label is opaque, only the portion of the label that lies on the nearside of the label to the imaging device is visible to the imaging device as the portion of the label that lies on the far side of the cylinder will be obscured by the nearside portion. It is therefore desirable to identify and remove those pixels from the label space that are not visible in the imaged label space. To do this, it can be assumed that, when viewing a cylindrical container, its long edges as they appear in the image define a plane that bisects the cylinder, dividing it into a visible section and an obscured section. Accordingly, this divides the label space into the part of the label that is visible and the part of the label that is obscure, as shown in FIG. 12. The long edges of the cylinder may be identified among the points of the mapping in the imaged label space using simple edge detection and, since the distance between the imaging device and the imaged label is known for each point in the imaged label space, the label pixels that map to the far half of the container can be discarded. For set ups where mirrors are employed so that images received by imaging devices contain not only directly imaged representations of the drug-containing vessel, but also reflected images of the drug-containing vessel, the mappings are customised. For example, in the set-up of FIG. 10, each imaging device 1010, 1012 will acquire an image with a direct representation of the drug-containing vessel 1014 and also a reflected image of the drug-containing vessel 1014 that has been reflected from the respective mirrors 1016, 1018. Accordingly, as each image captured by the imaging device contains two representations of the drug-containing vessel 1014, two different mappings may be applied to each image so as to extract the information associated with each view of the drug-containing vessel 1014. Once information from the various views has been extracted, and unfurled then the various unfurled images may be patched together.

Figure 14:
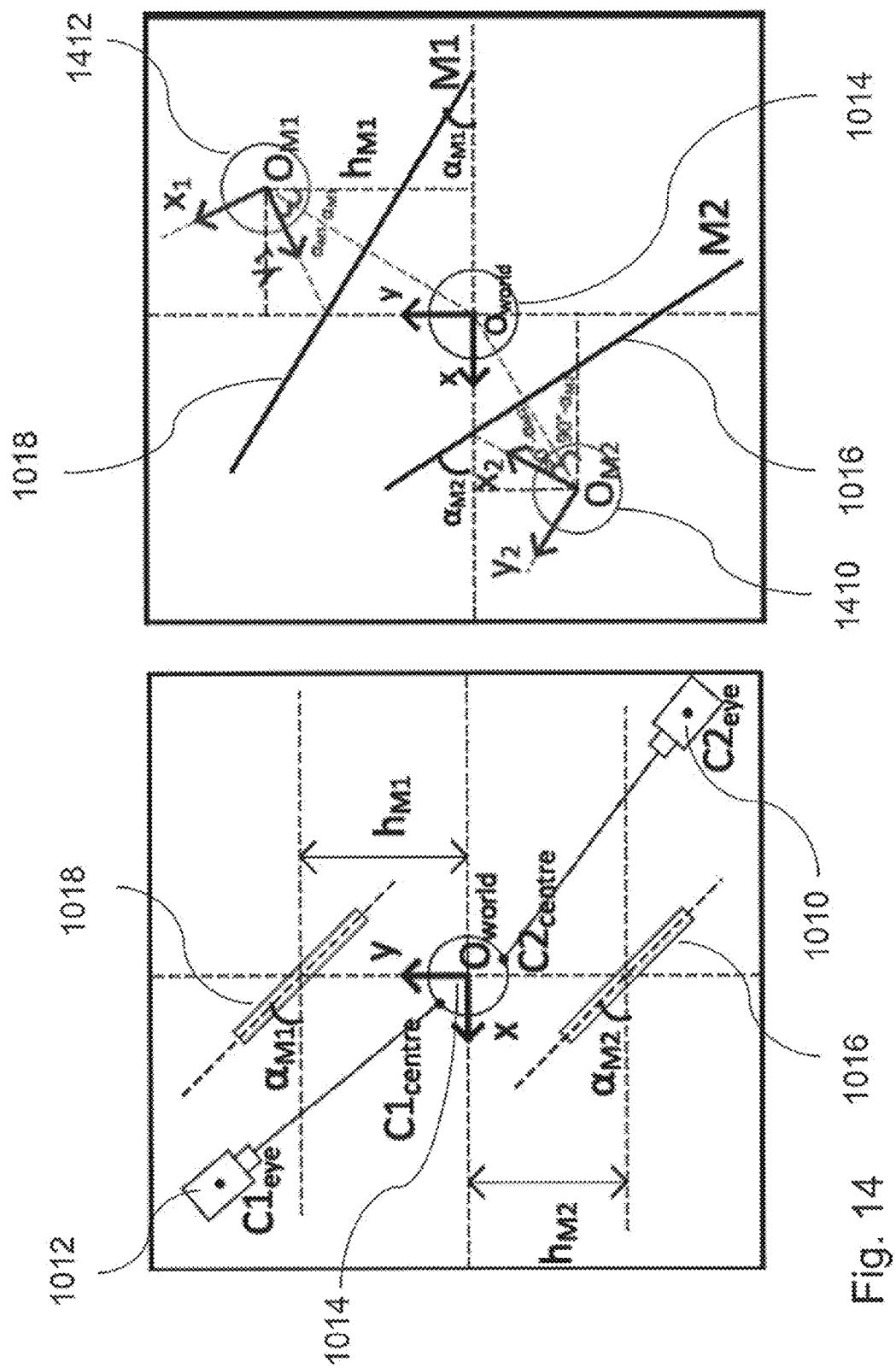
FIG. 14 shows a number of reconstructed label patches.

Continuing with the example set up of FIG. 10, FIG. 14 shows, on the left hand side, imaging devices 1010 and 1012 directly viewing the drug-containing vessel 1014. On the right hand side of FIG. 14, the angle of the reflecting mirrors 1016 and 1018 has been shown in an exaggerated manner to emphasise that each of the imaging devices 1010 and 1012 will, in addition to directly imaging the drug-containing vessel 1014, also image reflected images 1410, 1412 of the drug-containing vessel 1014. The parameters used to describe this particular setup are:

C1eye, C2eye: the (x,y,z) coordinates of camera 1 and camera 2 (expressed in the world coordinate system);
C1centre, C2centre: the (x,y,z) coordinates of the point at which the camera is looking (the optical centre). This are not unique, any point along the dotted line is suitable;
C1up, C2up: vectors used to compute the "up" direction of each camera; (0,1,0) if the camera is "right side up" and (0,−1,0) if the camera is upside down;
The vertical positions of the mirrors, $h_{M1}$ and $h_{M2}$ ($h_{M2}$ to be, considered negative);
The angles of the mirrors with a horizontal plane, $\alpha_{M1}$ and $\alpha_{M2}$.

These parameters, are measured on the apparatus and expressed in the world coordinate system. Measurements on the z axis may be less influential on accurate label reading and so it may be that a fixed length of cylinder is assumed, for example 40 mm, and it may be further assumed that the imaging devices are pointing towards the middle of it.

The setup of FIG. 10 provides four different pictures of the syringe from different angles. Four mappings are, therefore, required:

1. From label to image 1: Cylinder in the world coordinates, viewed by imaging device 1010;
2. From label to image 1: Cylinder in the mirror 1 coordinate system, viewed by imaging device 1010;
3. From label to image 2: Cylinder in the world coordinates, viewed by imaging device 1012;
4. From label to image 2: Cylinder in the mirror 2 coordinate system, viewed by imaging device 1012;

Mappings 1 and 3 can be accounted for by the model as previously described, by using different projection matrices for each of the imaging devices that are looking at the drug-containing vessel 1014. Mappings for the mirror images are performed by expressing the coordinates of the mirrored images in the same coordinate system as the original cylinder (considered the "world" coordinate system, to distinguish it from the imaging devices coordinate systems). This can be implemented in the same way as in above, but with an additional step of multiplying the vector of cylinder coordinates by a transformation matrix that aligns the mirror coordinate system with the world coordinate system. This transformation matrix will be denoted by M, and can be expressed as a function of the two mirror parameters, mirror angle and mirror vertical position; it resembles a homogenous rotation and translation matrix, but would not be considered a proper rotation matrix, as the mirror coordinate system does not follow the right hand rule anymore. Revising the mapping model to accommodate mirror images gives:

$$\begin{bmatrix} u \\ v \\ w \\ 1 \end{bmatrix} = PM \begin{bmatrix} x_{cyl} \\ y_{cyl} \\ z_{cyl} \\ 1 \end{bmatrix}, x_{photo} = \frac{u}{w}, y_{photo} = \frac{v}{w}$$

where $$M = \begin{bmatrix} \cos(2\alpha) & \sin(2\alpha) & 0 & -h\sin(2\alpha) \\ \sin(2\alpha) & -\cos(2\alpha) & 0 & h+h\cos(2\alpha) \\ 0 & 0 & 1 & 0 \\ 0 & 0 & 0 & 1 \end{bmatrix}$$

The mappings from the imaging device image to the label can be generated offline and encompass the image distortions that occur. A mapping is a pair of coordinates for each pixel (x,y) of the label: $map_x(x,y)$, which gives the x coordinate of the corresponding pixel in the photo, and $map_y(x,y)$, which gives the y coordinate. In other words, remapping performs the following assignment:

label(x,y)=photo($map_x(x,y),map_y(x,y)$)

Figure 15:
FIG. 15 shows four reconstructed image patches.

For the example of FIG. 10, two of the four mappings are applied to one of the two imaging device images and the other two mappings are applied to the other one of the two images. This results in four reconstructed patches of the label as shown in FIG. 15 which has a 3×2 matrix of images in which the first column shows the first and second imaging device images, the second column first row shows the reconstructed patch for the mirror reflection of the drug-containing vessel from the first imaging device image, the third column first row shows the reconstructed patch for the directly viewed drug-containing vessel from the first imaging device image, the second column second row shows the reconstructed patch for the mirror reflection of the drug-containing vessel from the second imaging device image, and the third column second row shows the reconstructed patch for the directly viewed drug-containing vessel from the second imaging device image. In examples where different numbers of imaging devices and/or mirrors are employed then the number of mappings will vary accordingly and so will the number of reconstructed patch images: for the apparatus of FIG. 4 the drug-containing vessel is viewed directly by two imaging devices and so two reconstructed patch images may be created; for the apparatus of FIG. 6 the drug-containing vessel is viewed directly once and two mirror images are viewed (all by the same imaging device) and so three reconstructed patch images may be created; for the apparatus of FIG. 9 a single imaging device captures four reflected images and so four reconstructed patch images may be created.

Figure 16:
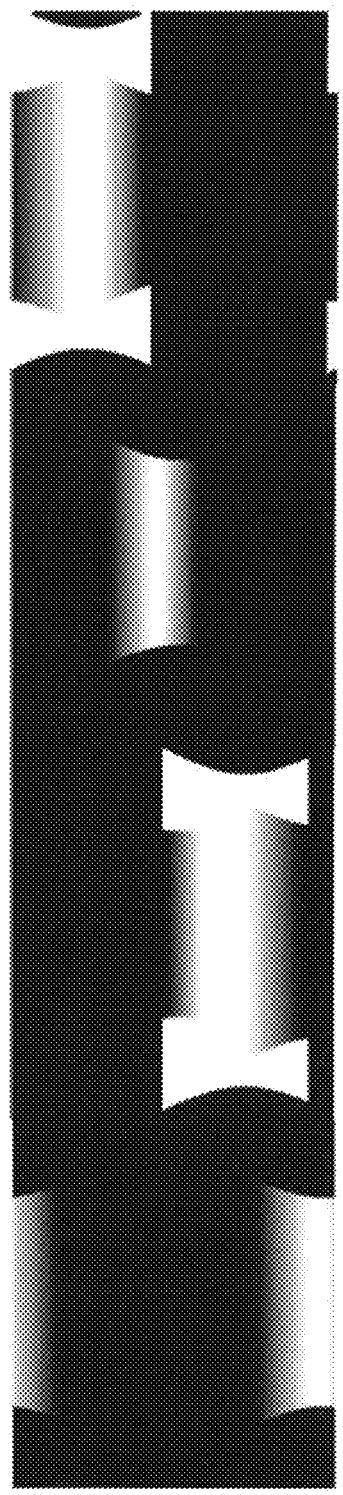
FIG. 16 shows four example masks corresponding to the mappings that respectively produced the reconstructed patches of FIG. 15.
Figure 17:
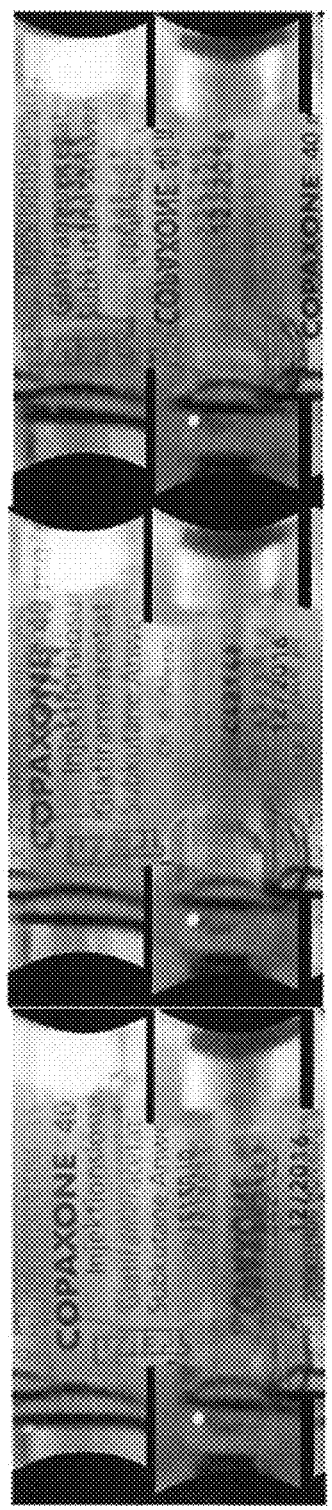
FIG. 17 shows three unfurled images following acquisition using the apparatus of FIG. 10.

In cases where multiple reconstructed patch images are created, they may be combined to form a single unfurled image of the label. Since each patch is at its correct location relative to the label, the problem of reassembly comes down to blending the different patches together. Blending is preferable since sometimes the same part of the label appears in multiple images, and due to this the reconstructed patch images may overlap. As one possibility, each patch is multiplied by a mask before adding it to the unfurled image of the label. Four example masks corresponding to the mappings that respectively produced the reconstructed patches of FIG. 15 is shown in FIG. 16 where white corresponds to 1 and black to 0. A person skilled in the art will recognize that different blending techniques may be employed and will be acquainted with suitable alternative blending techniques. FIG. 17 shows three unfurled images following acquisition using the apparatus of FIG. 10 and the above described processing.

In situations where the diameter of the drug-containing vessel is not known but can take a number of distinct specific potential values (i.e. a syringe of diameter 8 mm or 11 mm is expected), a mapping for each potential value can be used to create multiple unfurled images upon which subsequent processing can be performed. Such an approach avoids the need for dedicated processing to identify the size of the drug-containing vessel and instead performs the processing subsequently described herein on each unfurled image before taking the best individual label determination result as being indicative of the contents of the label.

Label Classification

The aim of the label classification step is to take each unfurled image and produce a decision about whether or not the label is of a pre-specified drug and/or dose.

One approach is to employ a template matching algorithm that searches for one or more given templates within the unfurled image. As an example, one of these templates can be the name of the drug and others will be used that correspond to the dose and other important or distinguishing features of the label.

Prior to performing the template matching, preprocessing approaches are applied to the unfurled images so as to improve classification performance by removing irrelevant information while preserving relevant information. These pre-processing steps make the template matching more robust and less computationally expensive.

Figure 18:
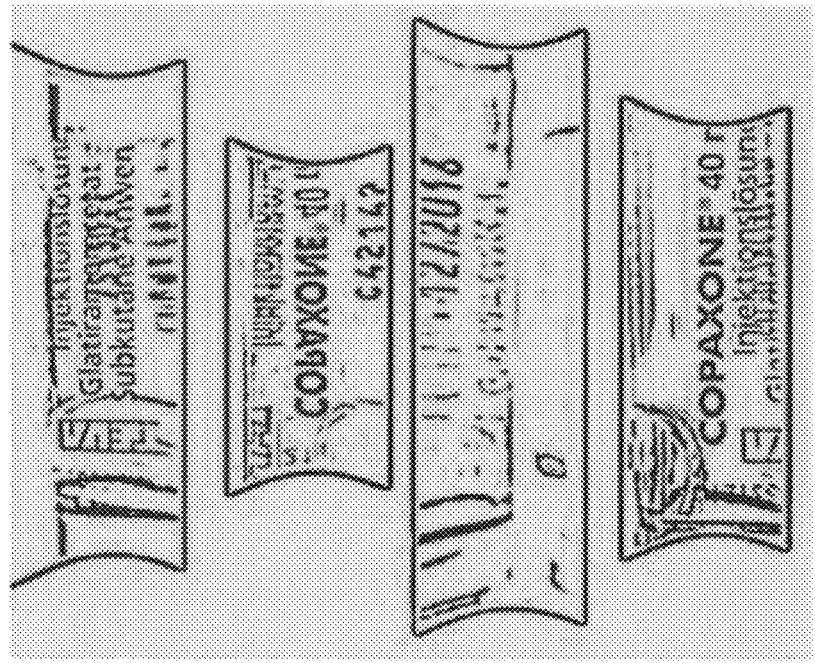
FIG. 18 shows an unfurled image on the left hand side and a binarised version of the unfurled image on the right hand side.
Figure 18:
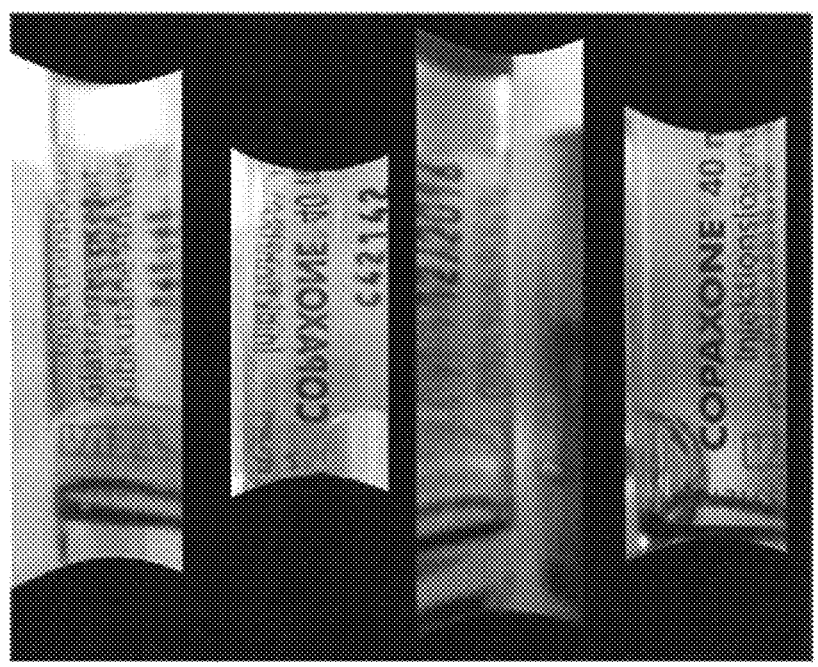

For many labels, the prime requirement for classification is to match the shape of the corresponding template to that label and ideally other factors would be ignored. As an example, lighting can cause considerable variations in the unfurled image. Accordingly, the pixel values of the unfurled images are thresholded to produce a binary image that removes such variation and returns a much simpler two-level image which is still classifiable. An example of such a binarised image is given in FIG. 18 which shows an unfurled image on the left hand side and a binarised version of the unfurled image on the right hand side.

Two approaches for performing binarisation will now be described. It may be that one or other of the approaches is more appropriate for a specific type of template. Where a drug or dosage is identified through the search for more than one template, then it may be necessary to calculate multiple (differently) binarised versions of the unfurled image so that the appropriate version is available for each template search.

In the below equations the following notation is employed: R, G and B are used to represent the red, green and blue values of a pixel. (x,y) is used to specify the specific location of a pixel in question. For example R(x,y) represents the red value of the pixel which is x pixels in from the left hand edge and y pixels down from the top. And F is used to represent the value of a pixel in the binarised image and is arranged so that F will always have a value of 0 or 1.

The first binarisation approach may be suitable for templates where pixels containing the text can be easily separated from the other pixels on the basis of intensity and involves first converting a colour unfurled image to greyscale. The greyscale value is calculated as a weighted sum of the RGB values:

$$I=0.2989R+0.5780G+0.1140B$$

The greyscale image is binarised by applying an adaptive thresholding algorithm although a skilled person will recognize other thresholding approaches that could equally be employed including, but not limited to, the use of a global threshold. For each pixel in the now greyscale unfurled image, the mean pixel value in a rectangular neighbourhood is calculated and subtracted from the pixel in question. A fixed threshold is then applied to the resulting image. This helps the thresholding to be robust to variations in lighting across the image. The local mean intensity for each pixel in the image is calculated by:

$$M(x, y) = \frac{1}{(2N+1)^2} \sum_{u=-N}^{N} \sum_{v=-N}^{N} I(x-u, y-v)$$

The binary value for each pixel is then set to:

$$F(x, y) = \begin{cases} 0 & \text{if } I(x, y) - M(x, y) < C \\ 1 & \text{if } I(x, y) - M(x, y) \geq C \end{cases}$$

The second binarisation approach may be suitable for templates where it is important to use colour information to distinguish which pixels belong to the text and which to the background. In such cases the unfurled image is, where needed, converted from RBG to HSV (HueSaturation-Value). The advantage of this representation is that the colour information is mostly contained in just the H value and this is relatively robust to varying degrees of lighting. The HSV representation of the unfurled image is then binarised by selecting the pixels whose H, S and V values lie within a given range, which is centred on the colour of the text:

$$F(x,y)=1 \text{ if } T_{min}^{H} \leq H(x,y) \leq T_{max}^{H} \text{ and } T_{min}^{S} \leq S(x,y) \leq T_{max}^{S} \text{ and } T_{min}^{V} \leq V(x,y) \leq T_{max}^{V}$$

Once the unfurled image has been binarised, a template matching approach is employed which slides a template around the binarised unfurled image and finds the point or points where the template best matches the binarised unfurled image by evaluating a similarity measure between the template and a number of candidate points in the binarised unfurled image. This can be considered an optimization process wherein potential template locations in the unfurled image are evaluated in order to determine a similarity score and the template location at which the similarity score is optimal (maximum or minimum depending on the similarity score) is searched for. Example optimisation approaches that could be employed would be to evaluate all possible template positions or to use a gradient descent approach; other optimization approaches could also be employed.

Where there may be an issue with varying colour and intensity of a colour unfurled image, binarisation of the unfurled image may be suitable. As another possibility, template matching on colour images may be used along with a suitable colour-employing similarity measure.

Template matching can be very robust to noise and is also tolerant to the image being slightly out of focus (unlike edge or corner detectors which can require sharp edges); accordingly, the choice of a template matching approach is sympathetic to the nature of the unfurled images. However, standard template matching is not so tolerant to rotations, scale factors, perspective distortions, and occlusions/missing parts of an image.

Non-template-based shape-matching, for example keypoint extraction and Generalized Hough Transform, tend to use a "voting" procedure, where certain matching points on a shape are found, and for each possible position and orientation of an object, a "vote" is taken. This has several advantages: it is robust to occlusions/missing parts of an image (by tolerating a certain number of missing votes); it is robust to small rotations and perspective distortions; and it can be made tolerant to larger rotations and perspective distortions. If the object corresponding to the template is not present in the image to which the voting procedure is applied, there may be a number of background "votes" from matches in portions of the image that do not relate to the object and so a minimum number of votes threshold is used to detect that an object is present in an image. However, for the unfurled images, the use of standard keypoint extraction features did not prove reliable.

Figure 19:
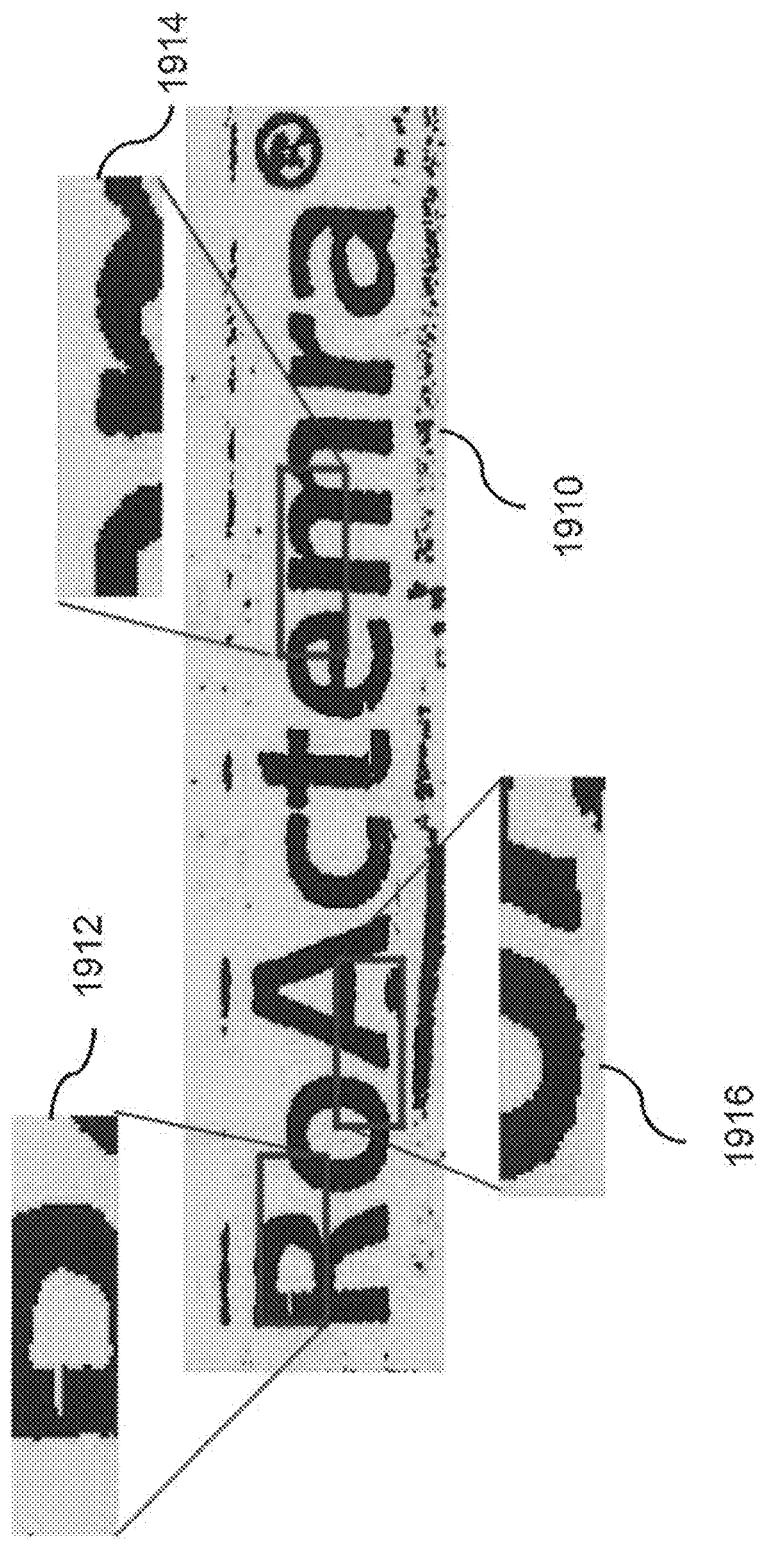
FIG. 19 shows a large template along with three sub-tiles thereof.

One approach is to combine a voting method with template matching by breaking up a template into smaller tiles and FIG. 19 shows a large template 1910, in this case of the label RoActemra® along with three small sub tiles thereof 1912, 1914, 1916. Although only three tiles are shown in FIG. 19 all, or substantially all, of the chosen template would preferably be covered by the tiles so that all, or substantially all, of the information contained within the template is also contained within the set of tiles. Template matching is then performed for tile in turn. Because each tile is small, the computational cost of processing all the tiles is similar to the cost of a full template match. Although any given tile may be found to be a best match at a location in the unfurled image that does not lie on the object represented by the template, it is unlikely that a plurality of matches that are close to the correct spatial arrangement will occur by chance.

Following template matching for each tile, each tile votes on where it thinks the "best" location is (mapped back to the centre of the original template) using the below-described approach which creates a voting image $V_t$ having the same dimensionality as the binarised image.

The voting algorithm takes as its inputs an image to test, I, and a set of binarised templates. As a preprocessing step, for each template, T, that template is divided into N tiles. In the follow description the subscript t is used to denote values that relate specifically to the $t^{th}$ tile. For each tile, its location relative to the top left hand corner of the full template is stored. f is the number of pixels between the left hand edge of the full template and the left hand edge of the tile. Likewise g is the number of pixels between the top edge of the full template and the top edge of the tile.

At run-time:
1. For each template
   a. For each tile in the current template i. Compute:

$$M_t(x-f, y-g) = \sum_{x',y'} T_t'(x', y') I'(x + x', y + y')$$

Where $$T_t'(x', y') = T_t(x', y') - \frac{1}{wh} \sum_{x'',y''} T_t(x'', y'')$$

and $$I'(x', y') = I(x', y') - \frac{1}{wh} \sum_{x'',y''} I(x' + x'', x' + y'')$$

where the summations are taken over the dimensions of the template and wh is a weighting factor and the response image $M_t$ is offset by an amount (f,g) to account for the relative position of the tile within the template.

The scores from the individual templates are combined in the following way. First the sub-template matching scores are converted to votes:

$$V_t = \begin{cases} 0 \text{ if } M_t < T_t \\ w_t \text{ if } M_t \geq T_t \end{cases}$$

Then the individual votes are summed:

$$V = \Sigma_{t=1}^{NT} V_t$$

Finally this is relaxed or blurred, in this case by convolving V with a square window. It is this final step that provides some scale and skew robustness by effectively allowing the different sub-templates to be moved slightly relative to one another:

$$S(x, y) = \sum_{u=-C}^{C} \sum_{v=-C}^{C} V(x-u, y-v)$$

The final score for the template is taken as the maximum value in the image S(x,y) and the template is deemed to be located at that point.

As one example, for getting a match between a template and the label of a syringe, the classification involves: splitting a 25×150 template into 30 patches of 5×25 and then, for each patch: computing the sum of squared differences at each possible position in the label so as to produce a score; determining the maximum score in a label, and setting a threshold at 90% of the determined maximum score; marking the positions in the label where the score is above the threshold with a 1 (and a 0 otherwise) and counting those positions (denote by N); giving each position marked a 1 a computed value of 1/N; summing, for each patch, the computed values of each of the positions in the label; and identifying the position having the highest summed value.

Figure 20:
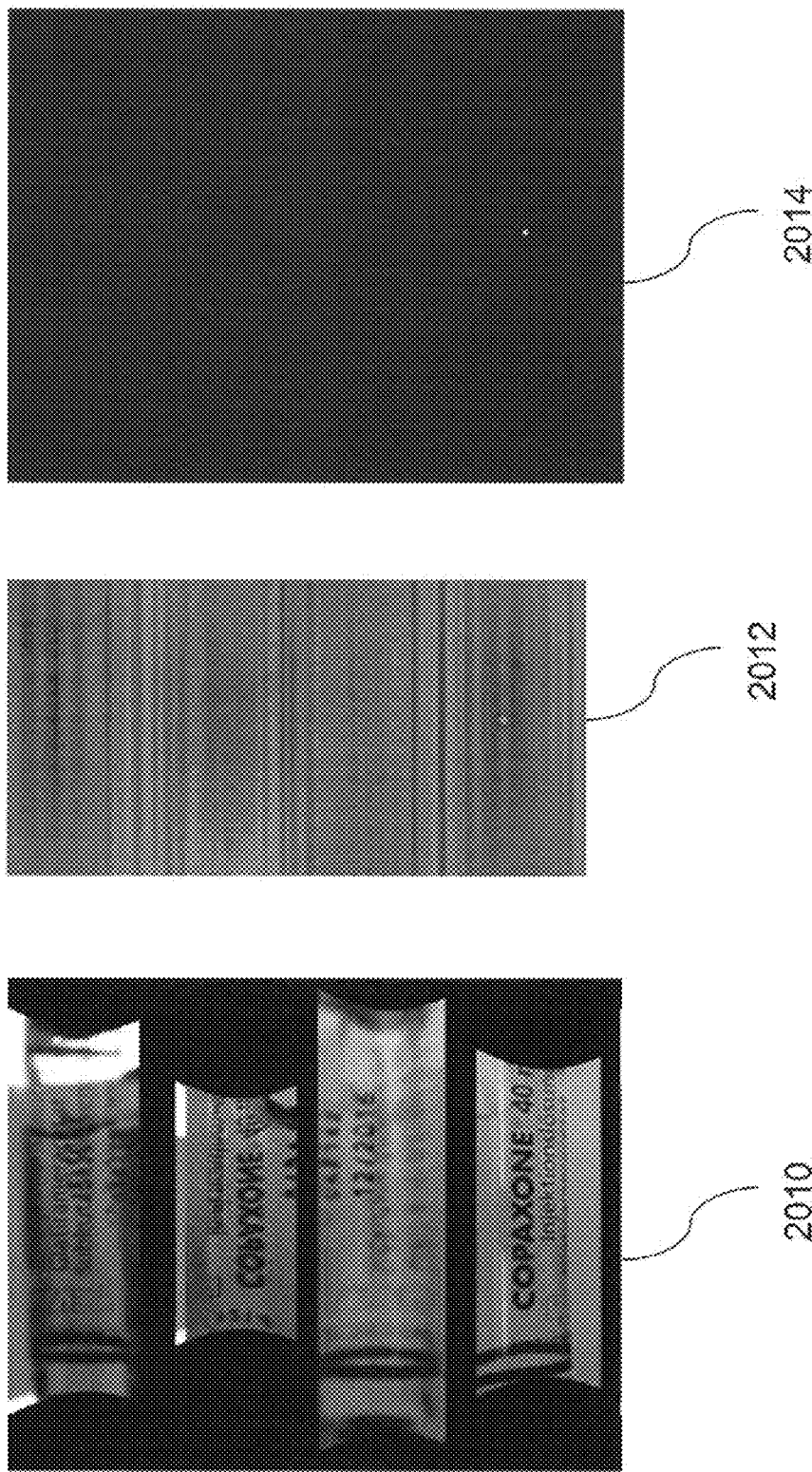
FIG. 20 shows an example unfurled image alongside a response for a standard template matching algorithm.

FIG. 20 shows an example unfurled image 2010, alongside a response for a standard template matching algorithm 2012 using a "COPAXONE" template and S(x,y) 2014 for the same template. It can be seen that S(x,y) 2014 shows a strong response at the correct location of the COPAXONE template.

Figure 21:
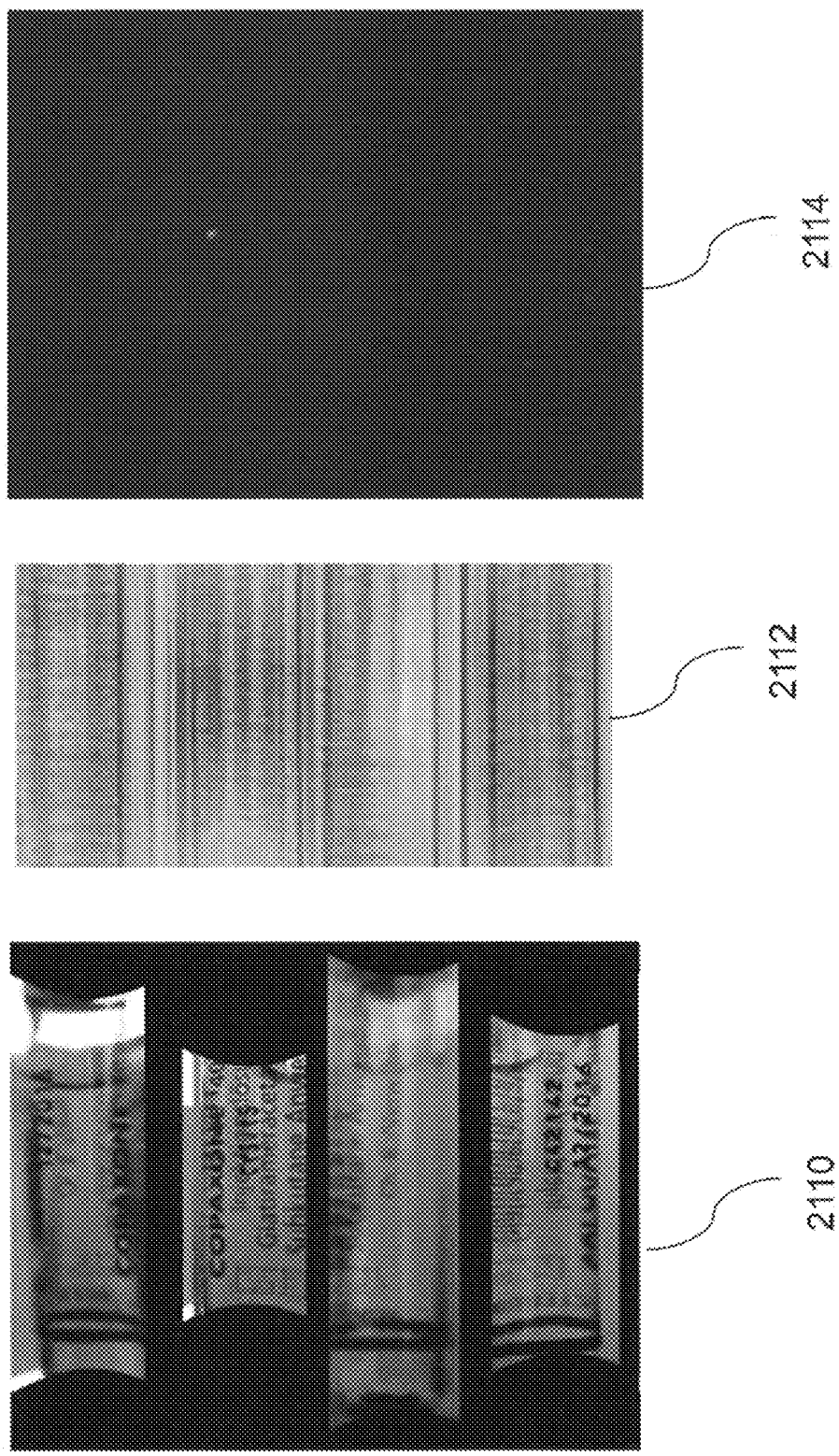
FIG. 21 shows another example unfurled image alongside a response for a standard template matching algorithm.

FIG. 21 shows another example unfurled image 2110, alongside a response for a standard template matching algorithm 2112 using a "COPAXONE" template and S(x,y) 2114 for the same template. It can be seen that the response for the standard template matching algorithm 2112 is a poor match to the template whereas S(x,y) 2114 shows a strong response at the correct location of the COPAXONE template. For the example of FIG. 21, there is some perspective distortion remaining in the unfurled image 2110, but in contrast to the standard template matching, the voting algorithm is tolerant to that. The peak is correspondingly less sharp, but still present.

Although the template matching approach described above works well for matching text, it is not so effective for cases where the template is a block of colour. As an example, for the drug Saizen blocks of colour provide valuable information about the drug-containing vessel as the label is yellow and has a yellow rectangle for a 20 mg cartridge and is red and has a red rectangle for a 12 mg cartridge. For such cases, instead of the template being chosen to represent writing on the label, it may instead be chosen to be a block of a given colour and size and template matching is then performed using sum of squared differences to calculate the quality of the template match. For colour block templates hue based binarisation was used. The colour binarisation processes were configured to accept a wide range of hues around the expected hue of the colour block. This was so that the identification was robust to a range of lighting conditions and would also mean that process would be robust to printing variations. This works well since blocks of uniform colour are quite robust to the perspective distortions that necessitate the voting based template matching scheme described above. Note that this template matching algorithm is applied to the colour image and not to a binarised version. For colour block templates, hue-based binarisation can be appropriate and the binarisation processes configured to accept a wide range of hues around the expected hue of the colour block. This makes the identification robust to a range of lighting conditions and also provides robustness in relation to printing variations.

Each label to be classified may have multiple templates associated with it. Examples of the types of template that a single label may have include: a template containing the name of the drug, a template containing text specifying the dose, a template of a block of colour that helps to identify the drug type or dose, a template containing features that are not expected to be present. Templates containing features that are not expected to be present can help make the classifier more robust in cases where there are known to be similar labels as looking for features that should not be present on a similar labels can help prevent the classifier from incorrectly accepting such labels.

Figure 22:
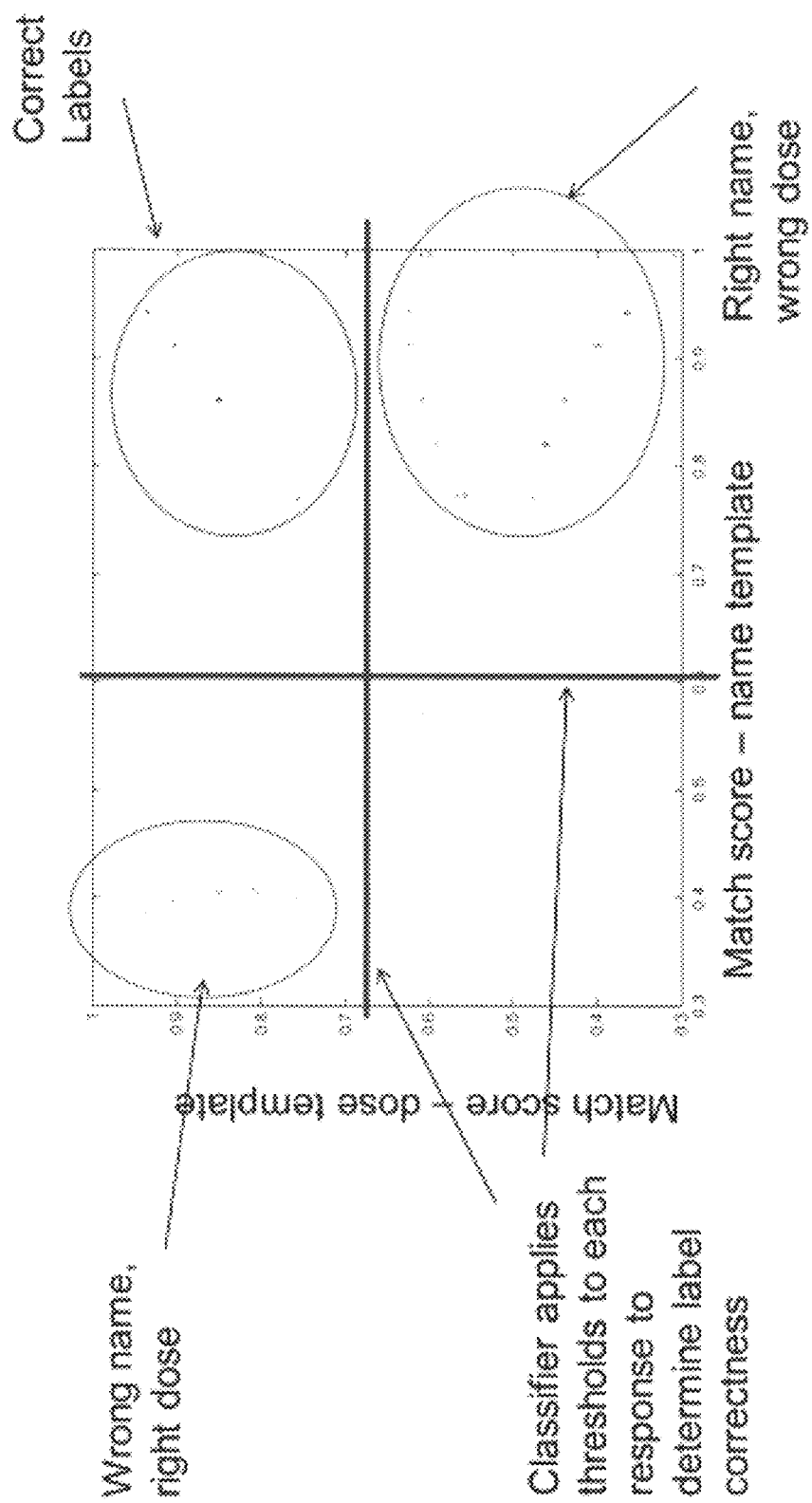
FIG. 22 illustrates a classification approach.

The unfurled image to be classified will produce a template matching score for each of the templates that are evaluated against it. These scores are then converted into a classification result. This is done by applying a threshold to each of the features and accepting the label if the template matching scores are above the threshold for each of the required templates and rejecting the label the label if the template matching scores are below the threshold for templates that should not be present as illustrated in FIG. 22.

As one possibility, in order to reduce computational complexity only a sub-region of the unfurled image may be searched when performing template matching. In particular, while the vertical position of the drug name could be anywhere, the horizontal position will only vary a small amount so the search may be constrained to occur within certain horizontal bounds—for example 10% of the image width around the expected horizontal position of the object represented by the drug name.

As one possibility, in order to reduce computational complexity, the resolution of the unfurled (or even imaging device) image(s) could be reduced. Although the results illustrated in FIGS. 20 and 21 were achieved for full resolution images, the approaches described herein could also be performed following an additional step of reducing the resolution of one or more of the imaging device image(s) and the unfurled image.

As one possibility, in order to reduce computational complexity, a cascaded approach could be employed wherein only a subset of the tiles (for example 3) are used during a first stage of the template matching so as to enable a quick initial estimation of the location of the template in the unfurled image before constrained template matching is performed with others of the tiles wherein the constrained template matching limits the distance from the initial estimate that the optimization is performed for the others of the tiles.

A large amount of the computational cost of the template matching approach comes from the fact that a large part of the image needs to be searched to find the part that contains the drug name. This comes from the fact that the drug-containing vessel may be in different rotational orientations. As one possibility, as the amount of dark pixels v light pixels in each row will vary with what is present in that part of the image, a metric of the dark pixels v light pixels in each row could be calculated and registered to the rotational orientation of the label that best matches the metric. The above described pattern matching would then be performed but, as the potential location drug name would be known to a much higher degree, a constrained template matching would be performed based on the registration thereby allowing the approach to perform whilst searching a much reduced portion the unfurled image.

The approaches described herein have been found to take in the range of 10 ms to 15 s and may take 200 ms to determine whether the label is of a given type and are estimated to require in the range of 0.05 mAh to 0.5 mAh and may take 0.06 mAh of processor and acquisition energy per label identification. When an apparatus arranged to perform the template matching approaches described herein needs to be able to recognize a new label, a new template can simply be supplied to the apparatus thereby enabling adaptation of the apparatus to recognize new labels without the need for a fundamental changing of the apparatus' processing code.

As one possibility, once an autoinjector has identified that it is carrying a particular drug-containing vessel, it may then proceed to permit injection from that drug-containing vessel. In cases where an autoinjector identifies that it is carrying a drug-containing vessel other than one that it is expecting to be carrying, it may issue a visual or audible alarm and/or disable its injection capabilities.

As one possibility, a light source is provided within the autoinjector and used to illuminate the curved surface of the cylindrical portion to help mitigate image processing issues caused by inconsistent illumination.

As one possibility, instead or, or as well as, using the above described template matching approach, a neural network based classification approach may be employed to identify the drug and/or details about the drug-containing vessel from the label image. An n×m pixel RGB image has a base dimensionality of 3 nm; so for a 2500×1900 image, this would result in an input vector of dimension of approximately 14 million. Accordingly the basic approach is to cut the unfurled image up into a set of smaller o×p image tiles (for example 15), compute a representative "feature" metric on each of these tiles, and then use this feature vector as input into the neural network. Preferably, the metric which will capture, with as few numbers as possible, the salient features of the tile which lend themselves to some degree of separation. For the metric on each tile, a guiding heuristic was to use one which would somehow capture both high frequency and low frequency characteristics. The metric chosen was a concatenation of data energy and the mean value of each of the three colour channels, which gives a metric dimension of 4. With this metric the size of the input vector becomes 4rs, and using a tiling dimension of 5×3 gives and input vector dimension of 60. This is close to a six order of magnitude reduction in the input vector size. The network used was a 60 input, one hidden layer, single output fully connected network. The size of the hidden layer is 20. One feature of the network was the use of a Gaussian activation function for the perceptrons in the hidden layer. The network was then trained on a set of training images for which the drug information is known.

Where mention is made herein to template matching, it is contemplated that, as one possibility, the medical device would be able to perform the template matching without the need to interrogate any external database. In such circumstances, the medical device may have stored in its memory one or more templates corresponding to candidate information about the vessel and/or the drug. Furthermore, although it may be beneficial for the template matching algorithm to learn from the matches that it makes and/or does not make, the template matching approach need not have any such learning capability.

It is contemplated that the imaging device or devices employed with the approaches described herein could be one or more cameras and so any use herein of the term "imaging device" could be replaced with the term "camera".

As one possibility, instead of the above described network architecture having only one output, which means it is unable to reject any images as being invalid. A multi-output network could instead be employed. One such topology could have eight (or more of less) outputs (one for each label category), with the expectation that for a given label there would be a high value on that label's output with all other outputs being low. Any output pattern which deviated from this pattern would then be interpreted as a rejection.

Although the approaches described herein may be employed with and implemented in any medical device, as one possibility, they may be implemented in a handheld medical device, such as an autoinjector. As another possibility, they may be implemented in a device that is not handheld such as a sharps bin.

In an approach described herein, information about a drug-containing vessel is determined by capturing image data of the curved surface of a cylindrical portion of a drug-containing vessel. The image data is unfurled from around the curved surface, binarised, and a template matching algorithm employed to determine that the label information comprises candidate information about the vessel and/or the drug.

As one possibility any of the approaches described herein may be employed in another approach wherein the label information is read from the unfurled image without using template matching—for example using text, bar code, QRS, and/or recognition approaches.

Methods described herein can be computer-implemented so as to be causable by the operation of a processor executing instructions. The approaches described herein may be embodied in any appropriate form including hardware, firmware, and/or software, for example on a computer readable medium, which may be a non-transitory computer readable medium. The computer readable medium carrying computer readable instructions arranged for execution upon a processor so as to make the processor carry out any or all of the methods described herein—thereby making such methods computer implemented.

The term computer readable medium as used herein refers to any medium that stores data and/or instructions for causing a processor to operate in a specific manner. Such a storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, any other magnetic data storage medium, a CD-ROM, any other optical data storage medium, any physical medium with one or more patterns of holes or protrusions, a RAM, a PROM, an EPROM, a FLASH-EPROM, NVRAM, and any other memory chip or cartridge.

The invention claimed is:

1. A computer-implemented method of determining information about a drug-containing vessel and/or the drug itself, wherein the vessel is located within a medical device and has a cylindrical portion bearing label information about the vessel and/or the drug, the method comprising:
    capturing, using one or more imaging devices contained within the medical device, image data of the curved surface of the cylindrical portion;
    creating a two-dimensional unfurled image from the image data by identifying where points in the unfurled image would map to on the curved surface if the unfurled image was furled about the curved surface;
    binarising the unfurled image;
    applying a template matching algorithm to the binarised image to determine the presence in the binarised image of one or more templates corresponding to candidate information about the vessel and/or the drug; and
    based on the determination of the presence in the binarised image of the one or more templates, determining that the label information comprises the candidate information,
wherein the template matching algorithm is arranged to evaluate each of the templates against the binarised image by evaluating a plurality of tile portions of the respective template against the binarised image, and
wherein, for each template, a voting image having the same dimensionality as the binarised image is created and its pixels populated based on votes from each of the plurality of tile portions of that template as to whether or not the evaluation of the respective tile portion was above or below a predetermined threshold for that pixel, and the maximum pixel value of each voting image is used to determine the presence in the binarised image of that template, and
wherein each voting image is blurred prior to determining its maximum pixel value.

2. The method of claim 1, further comprising, subsequent to creating the unfurled image and prior to binarising the unfurled image, performing a patching operation on the unfurled image to patch together portions of the image data that were captured by different ones of the one or more imaging devices.

3. The method of claim 1, wherein the creation of the two-dimensional unfurled image is performed so that the image data that was captured by each imaging device is only unfurled in respect of the portion of the curved surface of the cylindrical portion that was directly observable by that imaging device at the time of capturing.

4. The method of claim 1, wherein the binarising comprises:
    converting the unfurled image into a greyscale image; and
    creating the binarised image such that each pixel has a first value if the greyscale value of that pixel of the greyscale image data is less than a local mean intensity threshold and otherwise has a second value.

5. The method of claim 1, wherein the binarising comprises:
    converting the unfurled image into an Hue-Saturation-Value (HSV) image; and
    creating the binarised image such that each pixel has a first value if each of the Value-Hue-Saturation values of that pixel lie between respective Hue-Saturation-Value upper and lower thresholds and otherwise has a second value.

6. The method of claim 1, further comprising:
    applying a template matching algorithm to the unfurled image to determine the presence in the binarised image of one or more coloured templates corresponding to coloured candidate information about the vessel and/or the drug; and
    based on the determination of the presence in the unfurled image of the one or more coloured templates, determining that the label information comprises the coloured candidate information.

7. The method of claim 1, wherein the blurring of the voting image is achieved by convolving the voting image with a square window.

8. The method of claim 1, wherein the vessel is a syringe or cartridge.

9. The method of claim 1, further comprising using a light source within the medical device to illuminate the curved surface of the cylindrical portion.

10. A medical device arranged to perform the method of claim 1, wherein the one or more imaging devices are cameras.

11. A non-transitory computer readable medium comprising machine readable instructions arranged, when executed by one or more processors, to cause the one or more processors to carry out a computer-implemented method of determining information about a drug-containing vessel and/or the drug itself, wherein the vessel is located within a medical device and has a cylindrical portion bearing label information about the vessel and/or the drug, the method comprising:
    capturing, using one or more imaging devices contained within the medical device, image data of the curved surface of the cylindrical portion;
    creating a two-dimensional unfurled image from the image data by identifying where points in the unfurled image would map to on the curved surface if the unfurled image was furled about the curved surface;
    binarising the unfurled image;
    applying a template matching algorithm to the binarised image to determine the presence in the binarised image of one or more templates corresponding to candidate information about the vessel and/or the drug; and
    based on the determination of the presence in the binarised image of the one or more templates, determining that the label information comprises the candidate information,
wherein the template matching algorithm is arranged to evaluate each of the templates against the binarised image by evaluating a plurality of tile portions of the respective template against the binarised image, and
wherein, for each template, a voting image having the same dimensionality as the binarised image is created and its pixels populated based on votes from each of the plurality of tile portions of that template as to whether or not the evaluation of the respective tile portion was above or below a predetermined threshold for that pixel, and the maximum pixel value of each voting image is used to determine the presence in the binarised image of that template, and
wherein each voting image is blurred prior to determining its maximum pixel value.

* * * * *